United States Patent
Fain et al.

(10) Patent No.: US 9,801,684 B2
(45) Date of Patent: *Oct. 31, 2017

(54) SYSTEM AND METHOD FOR PERFORMING RENAL DENERVATION VERIFICATION

(71) Applicant: PACESETTER, INC., Sylmar, CA (US)

(72) Inventors: Eric S. Fain, Menlo Park, CA (US); Martin Cholette, Acton, CA (US); Gary R. Dulak, Moorpark, CA (US); Gene A. Bornzin, Simi Valley, CA (US); John W. Poore, South Pasadena, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/221,191

(22) Filed: Jul. 27, 2016

(65) Prior Publication Data
US 2016/0331453 A1    Nov. 17, 2016

Related U.S. Application Data

(63) Continuation of application No. 13/248,818, filed on Sep. 29, 2011.

(51) Int. Cl.
*A61B 18/14* (2006.01)
*A61N 1/36* (2006.01)
(Continued)

(52) U.S. Cl.
CPC ...... *A61B 18/1492* (2013.01); *A61B 5/04001* (2013.01); *A61B 5/7203* (2013.01);
(Continued)

(58) Field of Classification Search
CPC ............... A61N 1/0514; A61B 2018/00511
See application file for complete search history.

(56) References Cited

U.S. PATENT DOCUMENTS

| | | |
|---|---|---|
| 3,650,277 A | 3/1972 | Sjostrand et al. |
| 4,658,819 A | 4/1987 | Harris et al. |

(Continued)

FOREIGN PATENT DOCUMENTS

| | | |
|---|---|---|
| WO | 97/45157 | 12/1997 |
| WO | 00/66020 | 11/2000 |

(Continued)

OTHER PUBLICATIONS

Zazgornik, Jan et al, Bilateral Nephrectomy: The Best, but Often Overlooked, Treatment for Refractory Hypertension in Hemodialysis Patients, AJH 1998; 11:1364-1370.

(Continued)

*Primary Examiner* — Alyssa M Alter
(74) *Attorney, Agent, or Firm* — Armstrong Teasdale LLP

(57) ABSTRACT

A renal denervation feedback method is described that performs a baseline measurement of renal nerve plexus electrical activity at a renal vessel; denervates at least some tissue proximate the renal vessel after performing the baseline measurement; performs a post-denervation measurement of renal nerve plexus electrical activity at the renal vessel, after the denervating; and assesses denervation of the renal vessel based on a comparison of the baseline measurement and the post-denervation measurement of renal nerve plexus electrical activity at the renal vessel.

14 Claims, 7 Drawing Sheets

(51) Int. Cl.
*A61B 5/00* (2006.01)
*A61B 5/04* (2006.01)
*A61N 1/05* (2006.01)
*A61B 18/00* (2006.01)

(52) U.S. Cl.
CPC *A61N 1/36007* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01); *A61N 1/0551* (2013.01)

(56) References Cited

U.S. PATENT DOCUMENTS

| | | | |
|---|---|---|---|
| 5,035,694 | A | 7/1991 | Kasprzyk et al. |
| 5,255,679 | A | 10/1993 | Imran |
| 5,300,068 | A | 4/1994 | Rosar et al. |
| 5,368,591 | A | 11/1994 | Lennox et al. |
| 5,387,233 | A | 2/1995 | Alferness et al. |
| 5,465,717 | A | 11/1995 | Imran et al. |
| 5,531,779 | A | 7/1996 | Dahl et al. |
| 5,598,848 | A | 2/1997 | Swanson et al. |
| 5,607,462 | A | 3/1997 | Imran |
| 5,628,313 | A | 5/1997 | Webster, Jr. |
| 5,676,662 | A | 10/1997 | Fleischhacker et al. |
| 5,707,400 | A | 1/1998 | Terry, Jr. et al. |
| 5,769,077 | A | 6/1998 | Lindegren |
| 5,772,590 | A | 6/1998 | Webster, Jr. |
| 5,893,885 | A | 4/1999 | Webster, Jr. |
| 5,897,553 | A | 4/1999 | Mulier et al. |
| 5,954,649 | A | 9/1999 | Chia et al. |
| 5,954,719 | A | 9/1999 | Chen et al. |
| 6,004,269 | A | 12/1999 | Crowley et al. |
| 6,012,457 | A | 1/2000 | Lesh |
| 6,016,437 | A | 1/2000 | Tu et al. |
| 6,024,740 | A | 2/2000 | Lesh et al. |
| 6,073,048 | A | 6/2000 | Kieval et al. |
| 6,096,037 | A | 8/2000 | Mulier et al. |
| 6,117,101 | A | 9/2000 | Diederich et al. |
| 6,161,543 | A | 12/2000 | Cox et al. |
| 6,178,349 | B1 | 1/2001 | Kieval |
| 6,200,312 | B1 | 3/2001 | Zikorus et al. |
| 6,216,044 | B1 | 4/2001 | Kordis |
| 6,233,491 | B1 | 5/2001 | Kordis et al. |
| 6,283,951 | B1 | 9/2001 | Flaherty et al. |
| 6,287,608 | B1 | 9/2001 | Levin et al. |
| 6,292,695 | B1 | 9/2001 | Webster, Jr. et al. |
| 6,322,559 | B1 | 11/2001 | Daulton et al. |
| 6,460,545 | B2 | 10/2002 | Kordis |
| 6,522,926 | B1 | 2/2003 | Kieval et al. |
| 6,613,045 | B1 | 9/2003 | Laufer et al. |
| 6,616,624 | B1 | 9/2003 | Kieval |
| 6,635,054 | B2 | 10/2003 | Fjield et al. |
| 6,656,174 | B1 | 12/2003 | Hegde et al. |
| 6,669,655 | B1 | 12/2003 | Acker et al. |
| 6,699,231 | B1 | 3/2004 | Sterman et al. |
| 6,748,255 | B2 | 6/2004 | Fuimaono et al. |
| 6,805,131 | B2 | 10/2004 | Kordis |
| 6,845,267 | B2 | 1/2005 | Harrison et al. |
| 6,954,977 | B2 | 10/2005 | Maguire et al. |
| 6,970,730 | B2 | 11/2005 | Fuimaono et al. |
| 7,122,031 | B2 | 10/2006 | Edwards et al. |
| 7,149,574 | B2 | 12/2006 | Yun et al. |
| 7,155,284 | B1 | 12/2006 | Whitehurst et al. |
| 7,162,303 | B2 | 1/2007 | Levin et al. |
| 7,245,955 | B2 | 7/2007 | Rashidi |
| 7,291,146 | B2 | 11/2007 | Steinke et al. |
| 7,363,076 | B2 | 4/2008 | Yun et al. |
| 7,419,486 | B2 | 9/2008 | Kampa |
| 7,465,288 | B2 | 12/2008 | Dudney et al. |
| 7,468,062 | B2 | 12/2008 | Oral et al. |
| 7,481,803 | B2 | 1/2009 | Kesten et al. |
| 7,653,438 | B2 | 1/2010 | Deem et al. |
| 7,717,948 | B2 | 5/2010 | Demarais et al. |
| 7,742,795 | B2 | 6/2010 | Stone et al. |
| 7,756,583 | B2 | 7/2010 | Demarais et al. |
| 7,850,685 | B2 | 12/2010 | Kunis et al. |
| 7,949,407 | B2 | 5/2011 | Kaplan et al. |
| 8,145,316 | B2 | 3/2012 | Deem et al. |
| 8,224,416 | B2 | 7/2012 | de la Rama et al. |
| 8,343,213 | B2 | 1/2013 | Salahieh et al. |
| 8,347,891 | B2 | 1/2013 | Demarais et al. |
| 8,442,639 | B2 | 5/2013 | Walker et al. |
| 8,454,594 | B2 | 6/2013 | Demarais et al. |
| 8,545,495 | B2 | 10/2013 | Scheib |
| 9,022,948 | B2 | 5/2015 | Wang |
| 9,427,579 | B2* | 8/2016 | Fain .................. A61N 1/36007 |
| 9,439,598 | B2 | 9/2016 | Shimada et al. |
| 2002/0068885 | A1 | 6/2002 | Harhen et al. |
| 2002/0120304 | A1 | 8/2002 | Mest |
| 2003/0050681 | A1 | 3/2003 | Pianca et al. |
| 2003/0060858 | A1 | 3/2003 | Kieval et al. |
| 2003/0074039 | A1 | 4/2003 | Puskas |
| 2003/0114739 | A1 | 6/2003 | Fuimaono et al. |
| 2003/0216792 | A1 | 11/2003 | Levin et al. |
| 2003/0233099 | A1 | 12/2003 | Danaek et al. |
| 2004/0215186 | A1 | 10/2004 | Cornelius et al. |
| 2005/0288730 | A1 | 12/2005 | Deem et al. |
| 2006/0089678 | A1 | 4/2006 | Shalev |
| 2007/0135875 | A1 | 6/2007 | Demarais et al. |
| 2008/0255478 | A1 | 10/2008 | Burdette |
| 2009/0076409 | A1 | 3/2009 | Wu et al. |
| 2010/0016762 | A1 | 1/2010 | Thapliyal et al. |
| 2010/0094209 | A1 | 4/2010 | Drasler et al. |
| 2010/0168737 | A1 | 7/2010 | Grunewald |
| 2010/0249773 | A1 | 9/2010 | Clark et al. |
| 2010/0268307 | A1 | 10/2010 | Demarais et al. |
| 2010/0286684 | A1 | 11/2010 | Hata et al. |
| 2011/0004087 | A1 | 1/2011 | Fish et al. |
| 2011/0118726 | A1 | 5/2011 | de la Rama et al. |
| 2011/0137298 | A1 | 6/2011 | Nguyen et al. |
| 2011/0160720 | A1 | 6/2011 | Johnson |
| 2011/0213231 | A1 | 9/2011 | Hall et al. |
| 2011/0257641 | A1 | 10/2011 | Hastings et al. |
| 2011/0264011 | A1 | 10/2011 | Wu et al. |
| 2011/0264086 | A1 | 10/2011 | Ingle |
| 2011/0306851 | A1 | 12/2011 | Wang |
| 2012/0143097 | A1 | 6/2012 | Pike, Jr. |
| 2012/0143298 | A1 | 6/2012 | Just et al. |
| 2012/0296232 | A1 | 11/2012 | Ng |
| 2012/0323233 | A1 | 12/2012 | Maguire et al. |
| 2013/0116737 | A1 | 5/2013 | Edwards et al. |
| 2013/0131743 | A1 | 5/2013 | Yamasaki et al. |
| 2013/0144251 | A1 | 6/2013 | Sobotka |
| 2013/0172715 | A1 | 7/2013 | Just et al. |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012/106492 | 8/2012 |

OTHER PUBLICATIONS

Abboud, Francois M., The Sympathetic System in Hypertension, State-of-the-Art Review, Hypertension Journal of the American Heart Association, Hypertension 4 (suppl II): II-208-II-225, 1982.

Allen, Edgar V., Sympathectomy for Essential Hypertension, Circulation Journal of the American Heart Association, vol. VI, Jul. 1952, 131-140.

Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.

(56) References Cited

OTHER PUBLICATIONS

Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of the American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, Jan. 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.

Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013; 31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review—Part II, Journal of the National Medical Association, May 1948, vol. 40, No. 3., 113-116.
Dailey, U.G., Surgical Treatment of Hypertension: A Review—Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension A Systematic Review and Meta-Analysis, Journal of the American College of Cardiology, vol. 62, No. 3, Jul. 16, 2013, 231-241.
De Wardener, H.E., The Hypothalamus and Hypertension, Physiological Reviews,vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of the American Heart Association, vol. 13, No. 6, Part 1, Jun. 1989, 539-548.

(56) References Cited

OTHER PUBLICATIONS

Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of the American Heart Association, vol. 41, Mar. 2003, Part II, 621-624.
Robbins, Ivan M. et al, Pulmonary Vein Stenosis After Catheter Ablation of Atrial Fibrillation, Circulation Journal of the American Heart Association, 1998;98:1769-1775.
Rocha-Singh, Krishna J., Catheter-Based Sympathetic Renal Denervation A Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4): 94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of the American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of the American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention, May 2013; 9:R58-R66.
Sellers, Alfred M. et al, Adrenalectomy and Sympathectomy for Hypertension Ten Year Survival, Archives of Surgery, vol. 89, Nov. 1964, 880-886.
Ben, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.

Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of the American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of the American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following *KSR V. Teleflex*, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of the American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. And Exper.—Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.

(56) References Cited

OTHER PUBLICATIONS

Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Mazer, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of the American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of the American Heart Association, Jan. 28, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of the American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. Jul. 8, 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of the American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Grassi, Guido et al, Baroreflex Control of Sympathetic Nerve Activity in Essential and Secondary Hypertension, Hypertension Journal of the American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of the American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.
Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart, Sep. 15, 2013; 0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

(56) References Cited

OTHER PUBLICATIONS

Howell, Marcus H. et al, Tandem Stenting of Crossed Renal Arteries with Ostial Stenosis, Tex Heart Inst J. 2000; 27(2): 166-169.
Hoye, Neil A. et al, Endovascular Renal Denervation: A Novel Sympatholytic with Relevance to Chronic Kidney Disease, Clinical Kidney Journal Advance Access, Nov. 8, 2013; 0: 1-8.
Huang Shoei K. Stephen et al, Radiofrequency Catheter Ablation of Cardiac Arrhythmias, Basic Concepts and Clinical Applications, Wiley-Blackwell, Jun. 2000, 1-12.
Huang, Wann-Chu, Renal Denervation Prevents and Reverses Hyperinsulinemia-Induced Hypertension in Rats, Hypertension Journal of the American Heart Association, 1998;32:249-254.
Humpreys, Michael H., Renal Nerves and CKD: Is Renal Denervation the Answer?, Journal of the American Socity of Nephrology, 2012, 23: 1-3.
International Search Report and Written Opinion for Application No. PCT/US2010/054637 dated Jan. 3, 2011.
International Search Report and Written Opinion for Application No. PCT/US2010/054684 dated Jan. 10, 2011.
Irigoyen, M.C.C. et al, Baroreflex Control of Sympathetic Activity in Experimental Hypertension, Brazilian Journal of Medical and Biological Research, (1998) 31: 1213-1220.
Izzo, Jr, Joseph L. et al, The Sympathetic Nervous System and Baroreflexes in Hypertension and Hypotension, Current Hypertension Reports 1999, 3:254-263.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013; Nov. 28, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; Mar. 2013.

Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of the American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5, pp. 253-255.
Oral, Hakan et al, Pulmonary Vein Isolation for Paroxysmal and Persistent Atrial Fibrillation, Circulation Journal of the American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, Time Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14 (4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of the American Heart Association, 2000;102:2619-2628.
Parati, Gianfranco et al, The Human Sympathetic Nervous System: Its Relevance in Hypertension and Heart Failure, European Heart Journal (2012) 33, 1058-1066.

(56) References Cited

OTHER PUBLICATIONS

Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, 10-15, Jan. 2002.
Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of the American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of the American Heart Association, 1999;99:319-325.
Plouin, Pierre-Francois et al, Blood Pressure Outcome of Angioplasty in Atherosclerotic Renal Artery Stenosis A Randomized Trial, Hypertension Journal of the American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System An Overview of Structure and Function, Journal of Pharmacological and Toxicological Methods 44 (2000) 333-340.
Putney, John Paul, Are Secondary Considerations Still "Secondary"?:An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19-26, 2013:2029-30.
Kaltenbach, Benjamin et al, Renal Artery Stenosis After Renal Sympathetic Denervation, J Am Coll Cardiol. Dec. 25, 2012;60(25):2694-5.

Kaltenbach, Benjamin et al, Renal Sympathetic Denervation as Second-Line Therapy in Mild Resistant Hypertension: A Pilot Study, Catheterization and Cardiovascular Interventions 81:335-339; Feb. 2013.
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the SYMPLICITY HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of the American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.

(56) References Cited

OTHER PUBLICATIONS

Lambert Gavin W. et al, Health-Related Quality of Life After Renal Denervation in Patients With Treatment-Resistant Hypertension, Hypertension. 2012;60:1479-1484.

Lee Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

Leishman, A.W.D., Hypertension—Treated and Untreated, British Medical Journal, May 1959, 1361-1368.

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

Levin, Stephen, Ardian: Succeeding Where Drugs Fail Treating Hypertension in the Cath Lab, In Vivo: The Business & Medicine Report, vol. 27, No. 10, Nov. 2009.

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.

Luscher, Thomas F. et al, Renal Nerve Ablation After SYMPLICITY HTN-3: Confused at the Higher Level?; European Heart Journal, doi:10.1093/eurheartj/ehu195; May 14, 2014.

Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.

Mahfoud, Felix et al, Expert Consensus Document from the European Society of Cardiology on Catheter-Based Renal Denervation, European Heart Journal, Apr. 25, 2013; 34(28):2149-57.

Mancia, Giuseppe et al, Sympathetic Activation in the Pathogenesis of Hypertension and Progression of Organ Damage, Hypertension Journal of the American Heart Association, 1999, 34:724-728.

McGahan, John P. et al, History of Ablation, Tumor Ablation, 2005, pp. 3-16.

Medtronic, Inc., J.P. Morgan Healthcare Conference, Corrected Transcript, Jan. 13, 2014, Factset:Callstreet, www.callstreet.com.

Medtronic, Inc. Medtronic Announces U.S. Renal Denervation Pivotal Trial Fails to Meet Primary Efficacy Endpoint While Meeting Primary Safety Endpoint, www.medtronic.com, Jan. 9, 2014.

Medtronic, Inc., RDN Therapy with the Symplicity Renal Denervation System, Procedure Fact Sheet, www.medtronic.com, 2011.

Medtronic, Inc., Renal Denervation (RDN) Novel Catheter-based Treatment for Hypertension, Symplicity RDN System Common Q&A, 2011.

Medtronic, Inc., Scientific Basis Behind Renal Denervation for the Control of Hypertension, Dec. 2012, http://www.icimeeting.com/2012/images/stories/PDF/1448_Wilcox_I_Mon.pdf.

Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.

Meredith, I T et al, Exercise Training Lowers Resting Renal But Not Cardiac Sympathetic Activity in Humans; Hypertension Journal of the American Heart Association, 1991;18:575-582.

Michaelis, Lawrence L. et al, Effects of Renal Denervation and Renin Depletion on the Renal Responses to Intravascular Volume Expansion, Ann Surg. Mar. 1972; 175(3): 424-430.

Millard, F.C. et al, Renal Embolization for Ablation of Function in Renal Failure and Hypertension, Postgraduate Medical Journal (1989) 65, 729-734.

\* cited by examiner

SYSTEM AND METHOD FOR PERFORMING RENAL DENERVATION VERIFICATION

CROSS-REFERENCE TO RELATED APPLICATIONS

This application is a continuation application of U.S. patent application Ser. No. 13/248,818, filed on Sep. 29, 2011, the entire contents and disclosure of which are hereby incorporated herein by reference in their entirety.

BACKGROUND OF THE INVENTION

The present invention relates generally to denervation, and more specifically to systems and methods for renal denervation verification and feedback.

Hypertension (HTN), or high blood pressure (HBP), is defined as a consistently elevated blood pressure (BP) greater than or equal to 140 mmHg systolic blood pressure (SBP) and 90 mmHg diastolic blood pressure (DBP). Hypertension is a "silent killer" that is not associated with any symptoms and in 95% of cases (primary hypertension) the specific cause is unknown. In the remaining 5% of patients (secondary hypertension), specific causes including chronic kidney disease, diseases of the adrenal gland, coarctation of the aorta, thyroid dysfunction, alcohol addiction, pregnancy or the use of birth control pills are present. In secondary hypertension, when the root cause is treated, blood pressure usually returns to normal.

Hypertension is a disease that affects 74.5 million patients in the US with 24% or 17.7 million patients classified as uncontrolled hypertensive patients. Of these 17.7 million US patients, 27% of them are resistant to drug therapy without any secondary causes. This equates to 4.8 million patients in the US and an estimated 12.4 million patients outside of the US for a total of 17.2 million patients worldwide. Needless to say, there is a need for additional therapeutic options for this class of unsuccessfully treated patients.

It is generally accepted that the causes of hypertension are multi-factorial, with a significant factor being the chronic hyper-activation of the sympathetic nervous system (SNS), especially the renal sympathetic nerves. Renal sympathetic efferent and afferent nerves, which lie in the wall of the renal artery, have been recognized as a critical factor in the initiation and maintenance of systemic hypertension. Renal arteries, like all major blood vessels, are innervated by perivascular sympathetic nerves that traverse the length of the arteries. The perivascular nerves consist of a network of axons, terminals, and varicosities, which are distributed mostly in the medial-adventitial and adventitial layers of the arterial wall.

Signals coming in to the kidney travel along efferent nerve pathways and influence renal blood flow, trigger fluid retention, and activate the renin-angiotensin-aldosterone system cascade. Renin is a precursor to the production of angiotensin II, which is a potent vasoconstrictor, while aldosterone regulates how the kidneys process and retain sodium. All of these mechanisms serve to increase blood pressure. Signals coming out of the kidney travel along afferent nerve pathways integrated within the central nervous system, and lead to increased systemic sympathetic nerve activation. Chronic over-activation can result in vascular and myocardial hypertrophy and insulin resistance, causing heart failure and kidney disease.

Previous clinical studies have documented that denervating the kidney has a positive effect for both hypertension and heart failure patients. Journal articles published as early as 1936 review surgical procedures called either sympathectomy or splanchnicectomy, to treat severe hypertension. A 1953 JAMA article by Smithwick et al. presented the results of 1,266 cases of surgical denervation to treat hypertension. The results included radiographic evidence of hearts that had remodeled after the surgery, while also showing significant blood pressure declines. Additional articles published in 1955 and 1964 demonstrated that the concept of using renal denervation to lower blood pressure and treat heart failure was viable. However, given the highly invasive and traumatic nature of the procedure and the advent of more effective antihypertensive agents, the procedure was not widely employed.

More recently, catheter ablation has been used for renal sympathetic denervation. Renal denervation is a method whereby amplified sympathetic activities are suppressed to treat hypertension or other cardiovascular disorders and chronic renal diseases. The objective of renal denervation is to neutralize the effect of renal sympathetic system which is involved in arterial hypertension. The renal sympathetic efferent and afferent nerves lie within and immediately adjacent to the wall of the renal artery. Energy is delivered via a catheter to ablate the renal nerves in the right and left renal arteries in order to disrupt the chronic activation process. As expected, early results appear both to confirm the important role of renal sympathetic nerves in resistant hypertension and to suggest that renal sympathetic denervation could be of therapeutic benefit in this patient population.

In clinical studies, therapeutic renal sympathetic denervation has produced predictable, significant, and sustained reductions in blood pressure in patients with resistant hypertension. Catheters are flexible, tubular devices that are widely used by physicians performing medical procedures to gain access into interior regions of the body. A catheter device can be used for ablating renal sympathetic nerves in therapeutic renal sympathetic denervation to achieve reductions of blood pressure in patients suffering from renal sympathetic hyperactivity associated with hypertension and its progression. Renal artery ablation for afferent and efferent denervation has been shown to substantially reduce hypertension. See, e.g., Henry Krum et al., "Catheter-based renal sympathetic denervation for resistant hypertension: a multicentre safety and proof-of-principle cohort study," published online Mar. 30, 2009 at www.thelancet.com. Krum et al. recently reported average reductions of 27 mmHg SBP and 13 mmHg DBP in 34 patients with 12-month follow-up data. In addition, despite having an average SBP baseline of 177 mmHg, 44% of those patients reached controlled blood pressure of <140 mmHg.

SUMMARY

Embodiments of this invention provide renal denervation validation and feedback by detecting renal nerve activity and/or the lack thereof in order to precisely titrate the RF energy dose to achieve the desired renal denervation. The use of RF ablation for denervation is merely illustrative in this disclosure. Other denervation techniques can be used instead, as discussed below.

The first approach assesses the completeness of the renal denervation such as renal artery ablation by measuring the renal nerve plexus electrical activity on the distal side of the lesion site. This activity will be solely intrinsic since there is no external stimulation of the renal nerve plexus. The second approach assesses the completeness of the renal artery ablation by stimulating the renal nerve plexus on the proximal side of the lesion while recording the renal nerve plexus activity on the distal side of the lesion, or vice versa. The third approach verifies with a high degree of confidence that efferent and afferent renal artery nerves have been disconnected. This is accomplished by applying stimulus at a first position in a renal artery and verifying that nerve conduction has been interrupted by evaluating a filtered, detected signal at a second position, and then repeating the procedure with stimulation and detection positions swapped. These approaches are illustrative but not limiting.

Embodiments of the present invention provide a feedback mechanism to control renal denervation (e.g., to titrate RF energy delivery for renal ablation). By assessing the denervation after ablation based on a baseline measurement, one can prevent excessive, unnecessary ablation or denervation. The denervation verification increases the response rate by ensuring that the renal nerve plexus is completely destroyed or at least adequately destroyed based on a preset threshold.

In accordance with an aspect of the present invention, a renal denervation feedback method comprises: performing a baseline measurement of renal nerve plexus electrical activity at a renal vessel; denervating at least some tissue proximate the renal vessel after performing the baseline measurement; performing a post-denervation measurement of renal nerve plexus electrical activity at the renal vessel, after the denervating; and assessing denervation of the renal vessel based on a comparison of the baseline measurement and the post-denervation measurement of renal nerve plexus electrical activity at the renal vessel.

In some embodiments, the method further comprises, if a target denervation of the renal vessel is not achieved, repeating the steps of denervating, performing a post-denervation measurement, and assessing denervation of the renal vessel until the target denervation of the renal vessel is achieved. Repeating the steps of denervating, performing a post-denervation measurement, and assessing denervation of the renal vessel comprises adjusting a level of denervation for denervating at least some tissue proximate the renal vessel based on result of assessing denervation of the renal vessel.

In specific embodiments, performing a baseline measurement comprises monitoring baseline afferent signals and baseline efferent signals at the renal vessel without external stimulation to the renal vessel, and performing a post-denervation measurement comprises monitoring post-denervation afferent signals and post-denervation efferent signals at the renal vessel without external stimulation to the renal vessel, after the denervating. Monitoring the baseline afferent signals and baseline efferent signals comprises monitoring baseline afferent compound action potential and baseline efferent compound action potential, counting a number of baseline afferent spikes each representing an afferent compound action potential that exceeds a preset threshold during a specified period of time, and counting a number of baseline efferent spikes each representing an efferent compound action potential that exceeds the preset threshold during the specified period of time. Monitoring the post-denervation afferent signals and post-denervation efferent signals comprises monitoring post-denervation afferent compound action potential and post-denervation efferent compound action potential, counting a number of post-denervation afferent spikes each representing an afferent compound action potential that exceeds the preset threshold during the specified period of time, and counting a number of post-denervation efferent spikes each representing an efferent compound action potential that exceeds the preset threshold during the specified period of time.

In some embodiments, the baseline measurement and the post-denervation measurement occur at a location of the renal vessel proximal of a kidney and proximal of a denervation location for denervating at least some tissue proximate the renal vessel, and the target denervation of the renal vessel is achieved when a ratio of the number of post-denervation afferent spikes to the number of post-denervation efferent spikes is below a preset threshold as compared to a ratio of the number of baseline afferent spikes to the number of baseline efferent spikes. The baseline measurement and the post-denervation measurement occur at a location of the renal vessel proximal of a kidney and distal of a denervation location for denervating at least some tissue proximate the renal vessel, and the target denervation of the renal vessel is achieved when a ratio of the number of post-denervation afferent spikes to the number of post-denervation efferent spikes is above a preset threshold as compared to a ratio of the number of baseline afferent spikes to the number of baseline efferent spikes.

In specific embodiments, performing a baseline measurement comprises supplying nerve stimulation to the renal vessel from one side of a denervation location for denervating at least some tissue proximate the renal vessel and measuring a baseline response of the renal vessel to the nerve stimulation on an opposite side of the denervation location, and performing a post-denervation measurement comprises supplying nerve stimulation to the renal vessel from one side of the denervation location and measuring a post-denervation response of the renal vessel to the nerve stimulation on an opposite side of the denervation location. The same nerve stimulation is supplied from a same first location on the same side of the denervation location for both the baseline measurement and the post-denervation measurement, and the response is recorded on a same second location on the same opposite side of the denervation location for both the baseline measurement and the post-denervation measurement.

In some embodiments, the nerve stimulation is supplied from the proximal side of the denervation location for both the baseline measurement and the post-denervation measurement, and the response is recorded on the distal side of the denervation location for both the baseline measurement and the post-denervation measurement. The nerve stimulation comprises one of electrical stimulation or pharmacological stimulation. Assessing denervation of the vessel comprises: computing a baseline parameter from the baseline response; computing a post-denervation parameter from the post-denervation response; and computing a degree of denervation as a ratio of the post-denervation parameter and the baseline parameter. The target denervation is achieved when the computed ratio falls within a preset range. The baseline parameter comprises a number of baseline spikes each representing a compound action potential that exceeds a preset threshold during a specified period of time as measured in the baseline response. The post-denervation parameter comprises a number of post-denervation spikes each representing a compound action potential that exceeds the same preset threshold during the same specified period of time as measured in the post-denervation response. The target denervation is achieved when the computed ratio falls below a preset number.

In specific embodiments, performing a baseline measurement comprises supplying nerve stimulation to the renal vessel from a first side of a denervation location for denervating at least some tissue proximate the renal vessel and measuring a first baseline response of the renal vessel to the nerve stimulation on a second side of the denervation location opposite the first side, and supplying nerve stimulation to the renal vessel from the second side and measuring a second baseline response of the renal vessel to the nerve stimulation on the first side, and performing a post-denervation measurement comprises supplying nerve stimulation to the renal vessel from the first side and measuring a first post-denervation response of the renal vessel to the nerve stimulation on the second side, and supplying nerve stimulation to the renal vessel from the second side and measuring a second post-denervation response of the renal vessel to the nerve stimulation on the first side. Performing a baseline measurement comprises supplying nerve stimulation to the renal vessel from a first location on the first side of the denervation location and measuring the first baseline response of the renal vessel to the nerve stimulation on a second location on the second side, and supplying nerve stimulation to the renal vessel from the second location and measuring the second baseline response of the renal vessel to the nerve stimulation at the first location. Performing a post-denervation measurement comprises supplying nerve stimulation to the renal vessel from the first location and measuring the first post-denervation response of the renal vessel to the nerve stimulation at the second location, and supplying nerve stimulation to the renal vessel from the second location and measuring the second post-denervation response of the renal vessel to the nerve stimulation at the first location.

In some embodiments, measuring the first baseline response comprises filtering the first baseline response to increase signal-to-noise ratio; measuring the second baseline response comprises filtering the second baseline response to increase signal-to-noise ratio; measuring the first post-denervation response comprises filtering the first baseline response to increase signal-to-noise ratio; and measuring the second post-denervation response comprises filtering the second baseline response to increase signal-to-noise ratio.

In specific embodiments, measuring the first baseline response comprises synchronizing with electrocardiogram to substantially avoid detected signals other than detected signals that are recorded during electrically quiet times; measuring the second baseline response comprises synchronizing with electrocardiogram to substantially avoid detected signals other than detected signals that are recorded during electrically quiet times; measuring the first post-denervation response comprises synchronizing with electrocardiogram to substantially avoid detected signals other than detected signals that are recorded during electrically quiet times; and measuring the second post-denervation response comprises synchronizing with electrocardiogram to substantially avoid detected signals other than detected signals that are recorded during electrically quiet times.

In some embodiments, measuring the first baseline response comprises epoch averaging of multiple epochs relative to stimulus of the nerve stimulation to increase signal-to-noise ratio; measuring the second baseline response comprises epoch averaging of multiple epochs relative to stimulus of the nerve stimulation to increase signal-to-noise ratio; measuring the first post-denervation response comprises epoch averaging of multiple epochs relative to stimulus of the nerve stimulation to increase signal-to-noise ratio; and measuring the second post-denervation response comprises epoch averaging of multiple epochs relative to stimulus of the nerve stimulation to increase signal-to-noise ratio.

In specific embodiments, the nerve stimulation is multi-phasic stimulation. The nerve stimulation is supplied via one or more electrodes made of low polarization electrode material. The nerve stimulation has a narrow pulse width selected to reduce stimulus polarization. The nerve stimulation has a pulse width substantially equal to chronaxie of the renal vessel.

In accordance with another aspect of the invention, a renal denervation feedback system comprises: at least one denervation member to denervate at least some tissue proximate the renal vessel; at least one measurement member to perform a baseline measurement of renal nerve plexus electrical activity at a renal vessel before denervation of at least some tissue proximate the renal vessel and to perform a post-denervation measurement of renal nerve plexus electrical activity at the renal vessel after the denervation; and a denervation assessment module to assess denervation of the renal vessel based on a comparison of the baseline measurement and the post-denervation measurement of renal nerve plexus electrical activity at the renal vessel.

In some embodiments, a denervation control module is configured, if a target denervation of the renal vessel is not achieved, to instruct operation of the at least one denervation member to repeat denervating at least some tissue proximate the renal vessel, instruct operation of the at least one measurement member to repeat performing a post-denervation measurement, and instruct the denervation assessment module to repeat assessing denervation of the renal vessel, until the target denervation of the renal vessel is achieved.

These and other features and advantages of the present invention will become apparent to those of ordinary skill in the art in view of the following detailed description of the specific embodiments.

DETAILED DESCRIPTION

Figure 1:
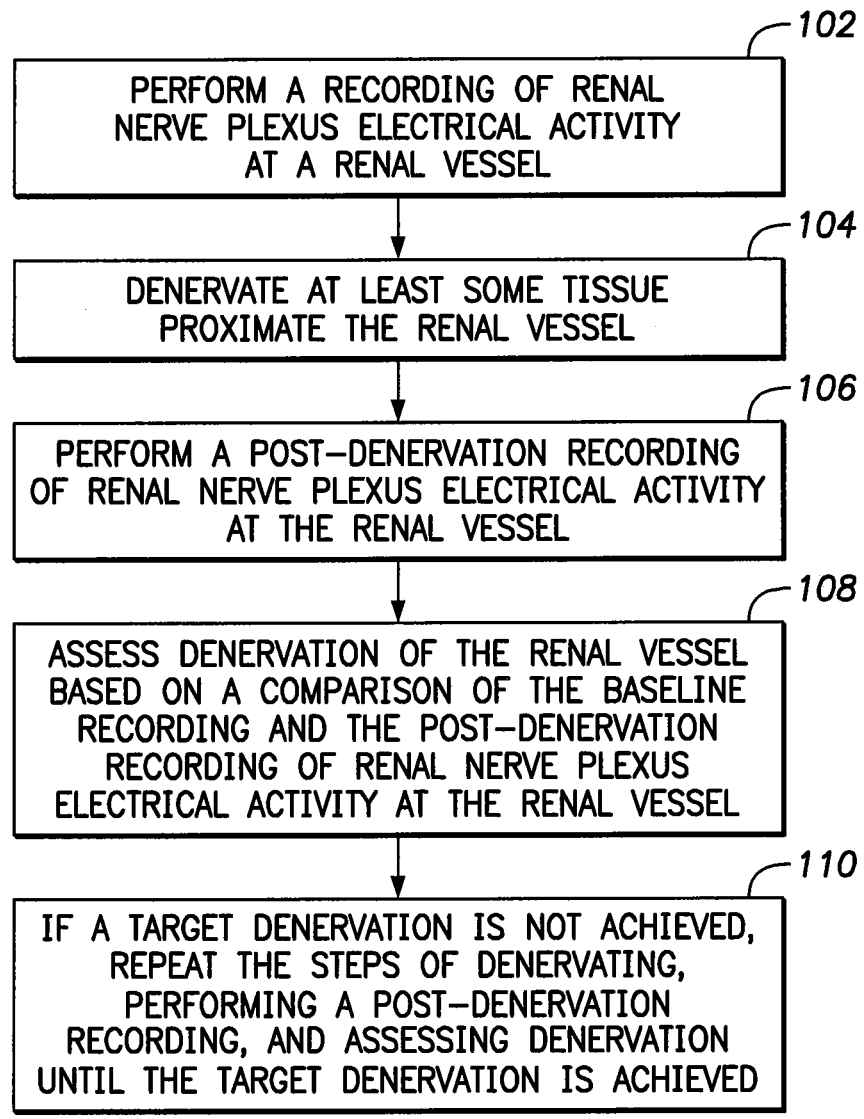
FIG. 1 is an example of a flow diagram illustrating the renal denervation verification and feedback method.

In the following detailed description, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment", "this embodiment", or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Furthermore, some portions of the detailed description that follow are presented in terms of algorithms, flow-charts and symbolic representations of operations within a computer. These algorithmic descriptions and symbolic representations are the means used by those skilled in the data processing arts to most effectively convey the essence of their innovations to others skilled in the art. An algorithm is a series of defined steps leading to a desired end state or result which can be represented by a flow chart. In the present invention, the steps carried out require physical manipulations of tangible quantities for achieving a tangible result. Usually, though not necessarily, these quantities take the form of electrical or magnetic signals or instructions capable of being stored, transferred, combined, compared, and otherwise manipulated. It has proven convenient at times, principally for reasons of common usage, to refer to these signals as bits, values, elements, symbols, characters, terms, numbers, instructions, or the like. It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "processing," "computing," "calculating," "determining," "displaying," or the like, can include the actions and processes of a computer system or other information processing device that manipulates and transforms data represented as physical (electronic) quantities within the computer system's registers and memories into other data similarly represented as physical quantities within the computer system's memories or registers or other information storage, transmission or display devices.

The present invention also relates to an apparatus for performing the operations herein. This apparatus may be specially constructed for the required purposes, or it may include one or more general-purpose computers selectively activated or reconfigured by one or more computer programs. Such computer programs may be stored in a computer-readable storage medium, such as, but not limited to optical disks, magnetic disks, read-only memories, random access memories, solid state devices and drives, or any other types of media suitable for storing electronic information.

The algorithms and displays presented herein are not inherently related to any particular computer or other apparatus. Various general-purpose systems may be used with programs and modules in accordance with the teachings herein, or it may prove convenient to construct a more specialized apparatus to perform desired method steps. In addition, the present invention is not described with reference to any particular programming language. It will be appreciated that a variety of programming languages may be used to implement the teachings of the invention as described herein. The instructions of the programming language(s) may be executed by one or more processing devices, e.g., central processing units (CPUs), processors, or controllers.

Exemplary embodiments of the invention, as will be described in greater detail below, provide apparatuses and methods for renal denervation verification and feedback.

FIG. 1 is an example of a flow diagram illustrating the renal denervation verification and feedback method. To provide feedback during a renal denervation procedure, the present method involves performing a baseline measurement of renal nerve plexus electrical activity at a renal vessel (step 102). The baseline measurement will be used to assess or verify the level of denervation so as to determine whether the target denervation is achieved or not. After performing the baseline measurement, at least some tissue proximate the renal vessel is denervated (step 104). The denervating typically involves electrical stimulation such as RF ablation, but may employ other methods, including the application of laser, high intensity focused ultrasound (HIFU), cryoablation, other thermal mechanisms for achieving ablation, or mechanical energy to sever or interrupt conduction of the nerve fibers. After the denervating, a post-denervation measurement of renal nerve plexus electrical activity at the renal vessel is performed (step 106). Denervation of the renal vessel is assessed based on a comparison of the baseline measurement and the post-denervation measurement of renal nerve plexus electrical activity at the renal vessel (step 108). The measurement may involve obtaining one or more parameters of the activity or event, such as amplitude, width, or the like, or any combination thereof. Alternatively, the measurement may involve recording or sampling many points to reconstruct an activity or event in time.

If a target denervation of the renal vessel is not achieved, the steps of denervating, performing a post-denervation measurement, and assessing denervation of the renal vessel are repeated until the target denervation of the renal vessel is achieved (step 110). In specific embodiments, this involves adjusting a level of denervation for denervating at least some tissue proximate the renal vessel based on result of assessing denervation of the renal vessel. For example, the RF ablation level can be adjusted based on the result of the denervation assessment.

To carry out the method, a renal denervation feedback system may include at least one denervation member to denervate at least some tissue proximate the renal vessel, at least one measurement member to perform a baseline measurement of renal nerve plexus electrical activity at a renal vessel before denervation of at least some tissue proximate the renal vessel and to perform a post-denervation measurement of renal nerve plexus electrical activity at the renal vessel after the denervation, and a denervation assessment module to assess denervation of the renal vessel based on a comparison of the baseline measurement and the post-denervation measurement of renal nerve plexus electrical activity at the renal vessel. In addition, a denervation control module may be provided, if a target denervation of the renal vessel is not achieved, to instruct operation of the at least one denervation member to repeat denervating at least some tissue proximate the renal vessel, instruct operation of the at least one measurement member to repeat performing a post-denervation measurement, and instruct the denervation assessment module to repeat assessing denervation of the renal vessel, until the target denervation of the renal vessel is achieved. Repeating the denervating, performing a post-denervation measurement, and assessing denervation of the renal vessel may include adjusting a level of denervation for denervating at least some tissue proximate the renal vessel based on result of assessing denervation of the renal vessel. The denervation assessment module and the denervation control module may be implemented in electronic circuitry or in software or firmware for execution by a processor, as discussed in further detail below. In the following, various examples of assessing or verifying denervation of the renal vessel are presented.

First Approach

According to a first approach, performing a baseline measurement includes monitoring baseline afferent and efferent signals at the renal vessel without external stimulation to the renal vessel, and performing a post-denervation measurement includes monitoring post-denervation afferent and efferent signals at the renal vessel without external stimulation to the renal vessel, after the denervating.

Figure 2:
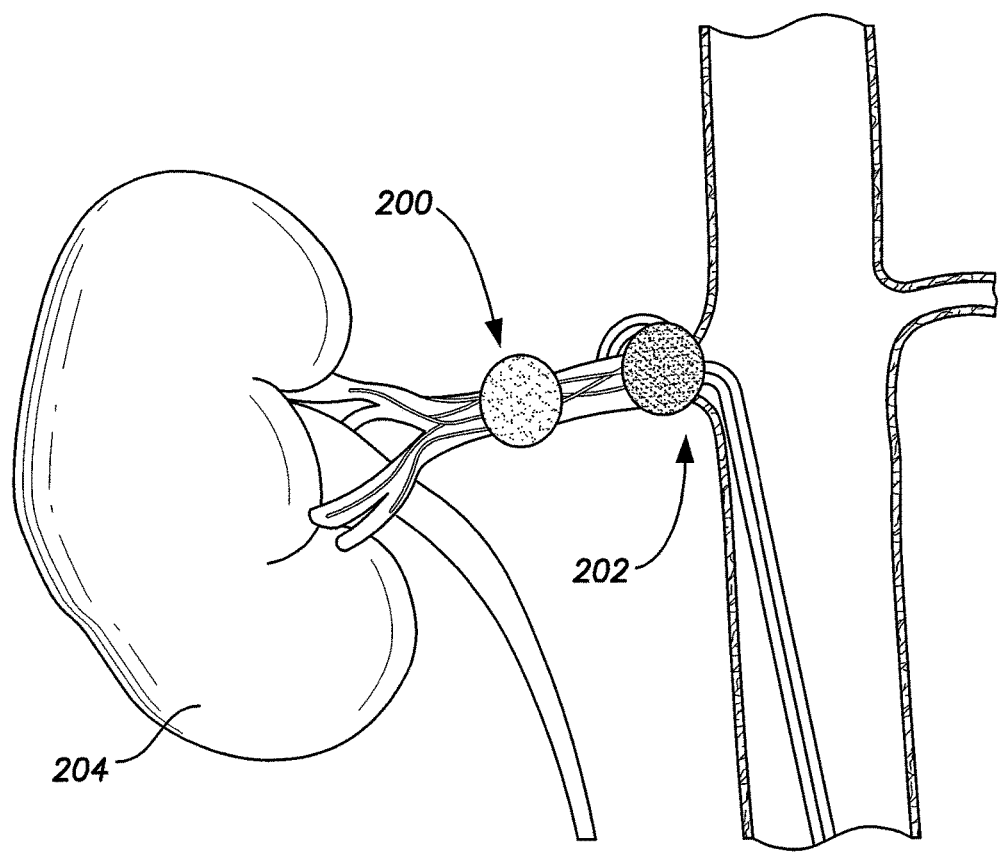
FIG. 2 shows an example of the renal denervation site and the measurement site according to a first approach for assessing denervation.

In a specific example, this approach assesses the completeness of the renal artery denervation or ablation by measuring the renal nerve plexus electrical activity on the distal side of the lesion site. FIG. 2 shows an example of the renal denervation site and the measurement site for assessing denervation. The measurement site 200 is distal of the denervation site 202 and is proximal of the kidney 204. If denervation is complete, this activity will be solely afferent since efferent signals will be blocked at the lesion site. As used herein, the "completeness" of the denervation or ablation may not require complete blockage of signals, but may indicate that a target level of denervation is reached, which can be predetermined or preset by a medical professional, for instance, based on clinical data or the like.

For the baseline measurement, a baseline test is made and the distal activity of the renal nerve plexus is recorded. This will become the baseline measurement. After performing the denervation or ablation of the renal artery plexus, a post-denervation test is made and the distal activity of the renal nerve plexus is recorded. In this example, a lesion completeness score is generated, which is equal to the ratio of a baseline score (baseline measurement) and a post-denervation score (post-denervation measurement). If the lesion completeness score exceeds a predetermined threshold; then the lesion is deemed complete; otherwise, the denervation is repeated and another lesion completeness score is generated until the predetermined threshold is met. The predetermined threshold can be determined in pre-clinical studies or the like.

Figure 3:
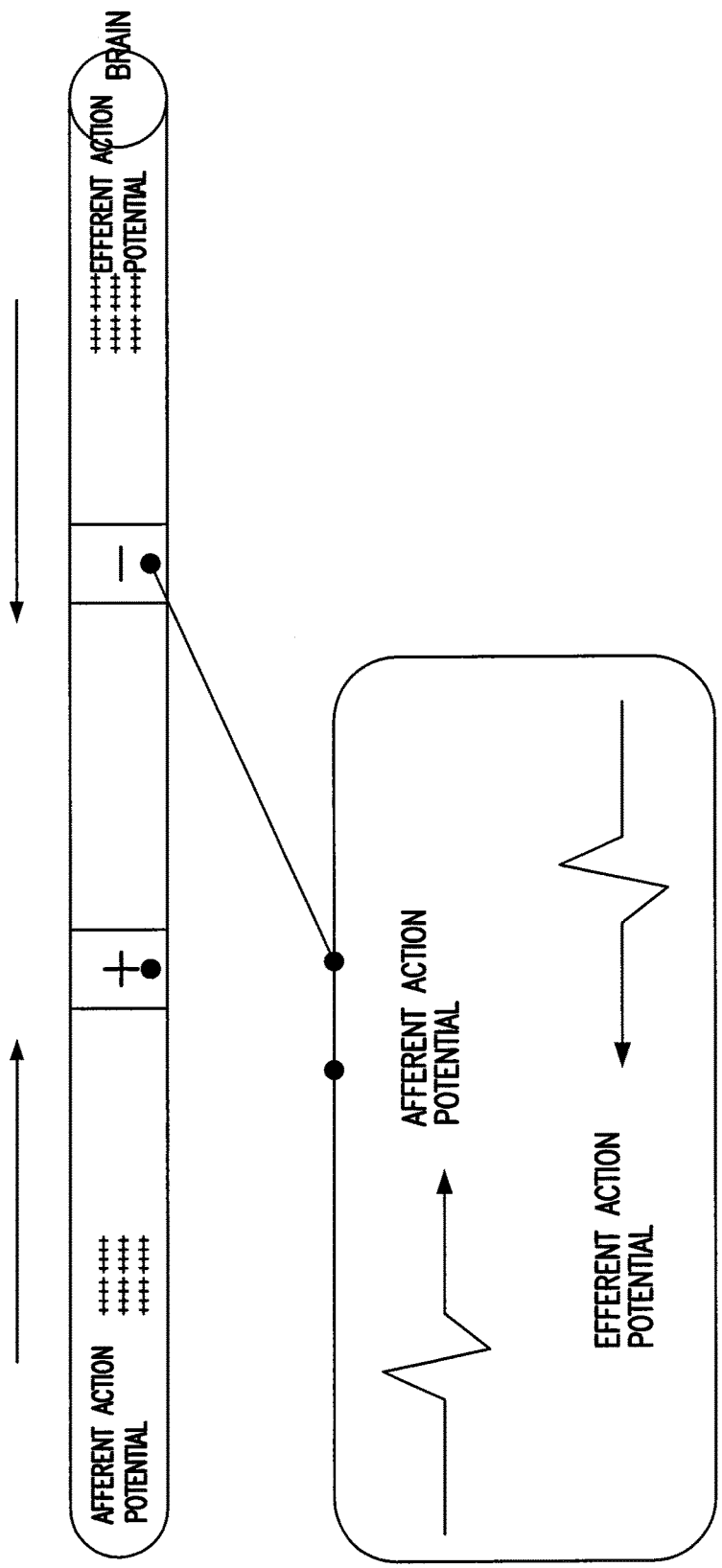
FIG. 3 shows an example of the afferent action potential and efferent action potential.

FIG. 3 shows an example of the afferent action potential and efferent action potential. The action potential direction between the brain and the kidney can be determined by looking at the morphological polarity of the electrogram. While both action potentials look alike as recorded on an oscilloscope, the phases are reversed polarity. The action potential direction can be determined by using bipolar measurement electrodes that are organized longitudinally at the measurement site 200.

There are various ways to quantify the nerve plexus activity. In one example, during each nerve activity measurement period (baseline or post-denervation), afferent and efferent "spikes" will be counted. Spikes represent compound action potential levels that meet or exceed a predetermined threshold level. The ratio of the number of afferent spikes and the number of efferent spikes will be computed for both periods and assigned as the lesion completeness score. That is, monitoring the baseline afferent signals and baseline efferent signals includes monitoring baseline afferent compound action potential and baseline efferent compound action potential, counting a number of baseline afferent spikes each representing an afferent compound action potential that exceeds a preset threshold during a specified period of time, and counting a number of baseline efferent spikes each representing an efferent compound action potential that exceeds the preset threshold during the specified period of time. Monitoring the post-denervation afferent signals and post-denervation efferent signals includes monitoring post-denervation afferent compound action potential and post-denervation efferent compound action potential, counting a number of post-denervation afferent spikes each representing an afferent compound action potential that exceeds the preset threshold during the specified period of time, and counting a number of post-denervation efferent spikes each representing an efferent compound action potential that exceeds the preset threshold during the specified period of time.

In one specific embodiment, the baseline measurement and the post-denervation measurement occur at a location of the renal vessel proximal of a kidney and distal of a denervation location for denervating at least some tissue proximate the renal vessel (as seen in FIG. 2). The target denervation of the renal vessel is achieved when a ratio of the number of post-denervation afferent spikes to the number of post-denervation efferent spikes is above a preset threshold as compared to a ratio of the number of baseline afferent spikes to the number of baseline efferent spikes.

In another specific embodiment, the baseline measurement and the post-denervation measurement occur at a location of the renal vessel proximal of a kidney and proximal of a denervation location for denervating at least some tissue proximate the renal vessel (e.g., by swapping the measurement site 200 and the denervation site 202 in FIG. 2). The target denervation of the renal vessel is achieved when a ratio of the number of post-denervation afferent spikes to the number of post-denervation efferent spikes is below a preset threshold as compared to a ratio of the number of baseline afferent spikes to the number of baseline efferent spikes.

Second Approach

According to a second approach, performing a baseline measurement includes supplying nerve stimulation to the renal vessel from one side of a denervation location for denervating at least some tissue proximate the renal vessel and measuring a baseline response of the renal vessel to the nerve stimulation on an opposite side of the denervation location, and performing a post-denervation measurement includes supplying nerve stimulation to the renal vessel from one side of the denervation location and measuring a post-denervation response of the renal vessel to the nerve stimulation on an opposite side of the denervation location. Examples of nerve stimulation include electrical stimulation and pharmacological stimulation such as the injection of neurotoxins.

Figure 4:
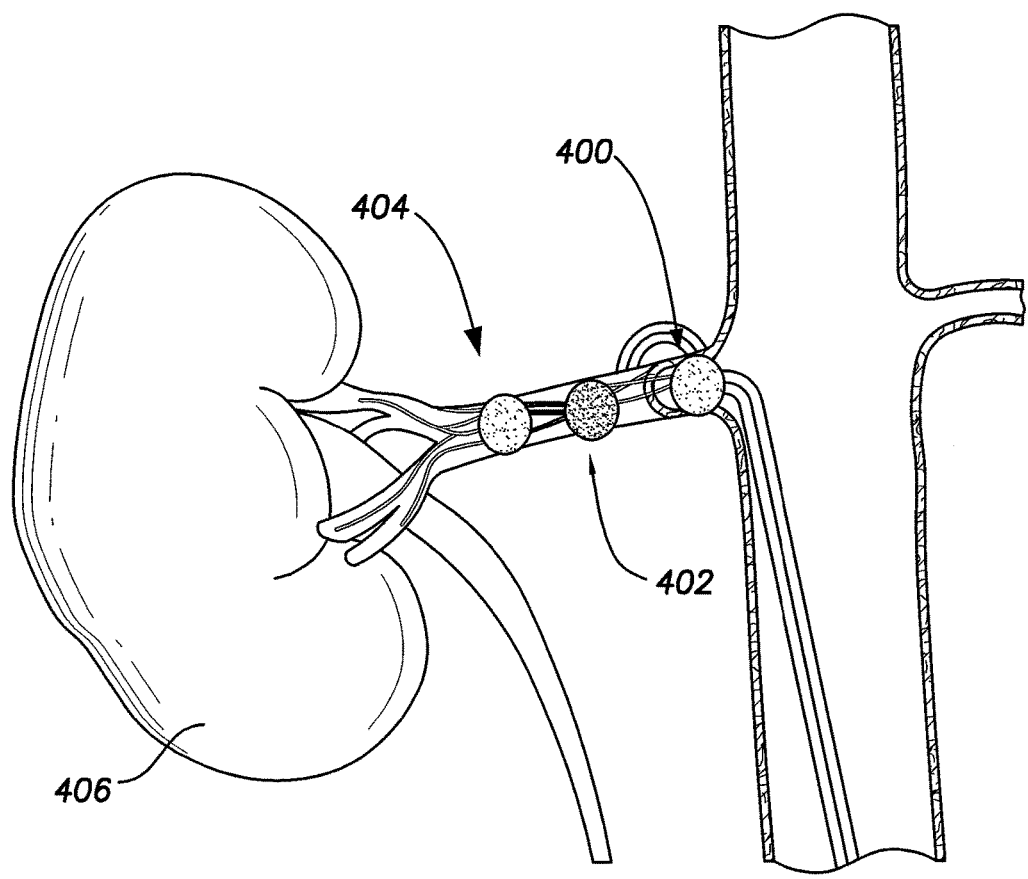
FIG. 4 shows an example of the renal denervation site, the stimulation site, and the measurement site according to a second approach of assessing denervation.

In a specific example, the method assesses the completeness of the renal artery denervation or ablation by stimulating the renal nerve plexus on the proximal side of the lesion while measuring the renal nerve plexus activity on the distal side of the lesion. FIG. 4 shows an example of the renal denervation site, the stimulation site, and the measurement site according to the second approach of assessing denervation. The stimulation site 400 is proximal of the denervation site 402, and the measurement site 404 is distal of the denervation site 402 and is proximal of the kidney 406. Before the denervation, a baseline test is made by stimulating the renal artery plexus and simultaneously measuring the distal activity. This will become the baseline measurement. After perform the denervation or ablation of the renal artery plexus, a post-denervation test is made by stimulating the renal artery plexus and simultaneously measuring the distal activity to obtain the post-denervation measurement. A lesion completeness score is generated as the ratio of the baseline score (baseline measurement) and the post-denervation score (post-denervation measurement). If the lesion completeness score exceeds a predetermined threshold, then the lesion is complete; otherwise, the denervation is repeated and another lesion completeness score is generated until the predetermined threshold is met. The predetermined threshold can be determined in pre-clinical studies or the like.

In one specific embodiment, the same nerve stimulation is supplied from the same first location on the same side of the denervation location for both the baseline measurement and the post-denervation measurement, and the response is recorded on the same second location on the same opposite side of the denervation location for both the baseline measurement and the post-denervation measurement (as seen in FIG. 4).

In another specific embodiment, the nerve stimulation is supplied from the proximal side of the denervation location for both the baseline measurement and the post-denervation measurement, and the response is recorded on the distal side of the denervation location for both the baseline measurement and the post-denervation measurement (as seen in FIG. 4).

Assessing denervation of the vessel includes computing a baseline parameter from the baseline response, computing a post-denervation parameter from the post-denervation response, and computing a degree of denervation as a ratio of the post-denervation parameter and the baseline parameter. The target denervation is achieved when the computed ratio falls within a preset range.

Figure 5:
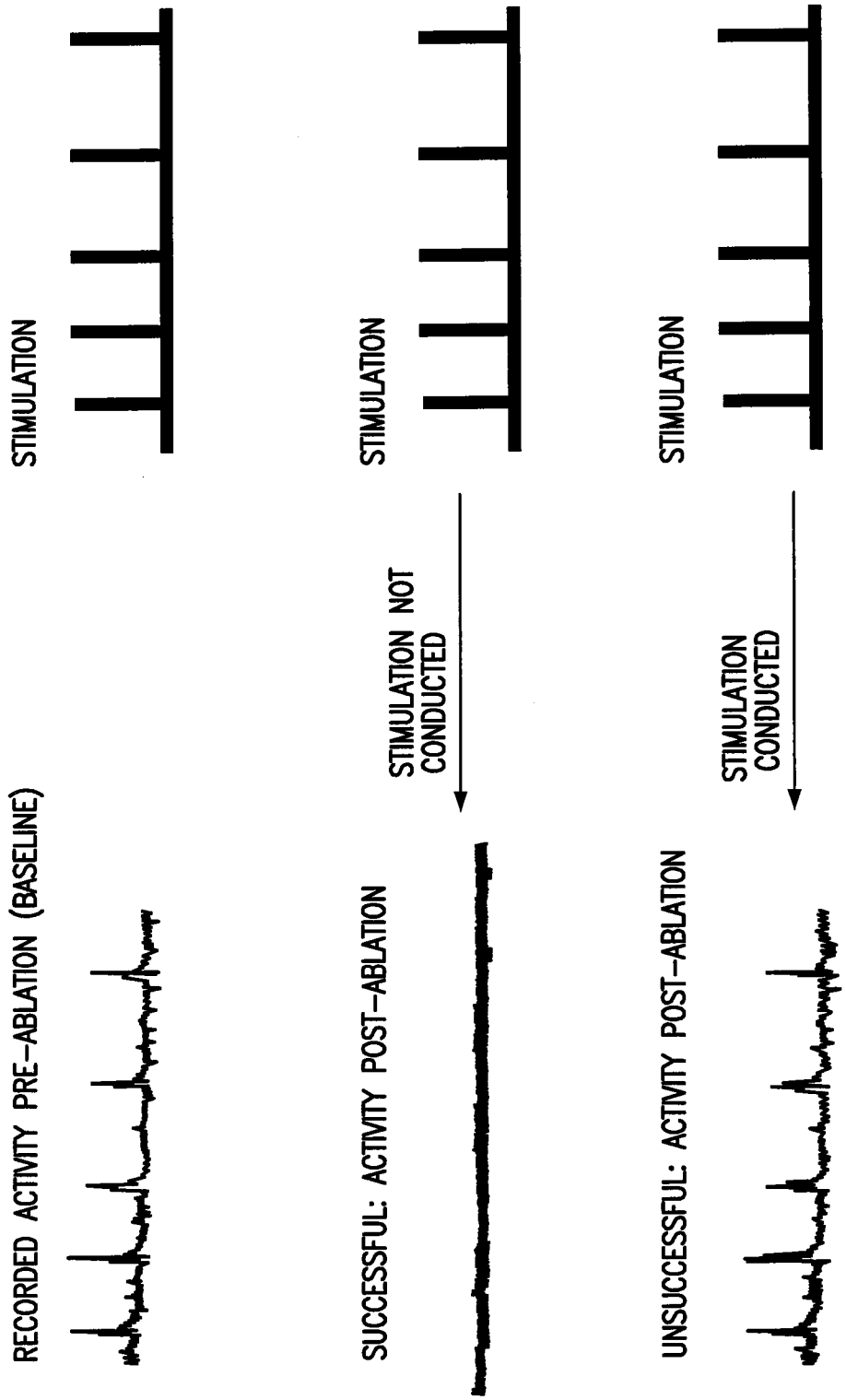
FIG. 5 shows an example of assessing nerve activity by counting spikes in response to stimulation.

There are various ways to quantify the nerve plexus activity. One way of assessing nerve activity is to count what are known as "spikes" during a specified period of time. Spikes represent compound action potential levels that meet or exceed a predetermined threshold level. FIG. 5 shows an example of assessing nerve activity by counting spikes in response to stimulation. The first recorded activity for the baseline measurement shows a number of spikes in response to the stimulation. The second recorded activity for the post-denervation measurement shows little or no spikes in response to the stimulation for a successful denervation, for which stimulation is not conducted or at least substantially not conducted after the denervating. The third recorded activity for the post-denervation measurement shows spikes in response to the stimulation for an unsuccessful denervation, for which stimulation is still conducted after the denervating.

In one example, the baseline parameter includes a number of baseline spikes each representing a compound action potential that exceeds a preset threshold during a specified period of time as measured in the baseline response. The post-denervation parameter includes a number of post-denervation spikes each representing a compound action potential that exceeds the same preset threshold during the same specified period of time as measured in the post-denervation response. The target denervation is achieved when the computed ratio falls below a preset number. The preset number can be determined by clinical studies or the like.

Third Approach

According to a third approach, performing a baseline measurement includes supplying nerve stimulation to the renal vessel from a first side of a denervation location for denervating at least some tissue proximate the renal vessel and measuring a first baseline response of the renal vessel to the nerve stimulation on a second side of the denervation location opposite the first side, and supplying nerve stimulation to the renal vessel from the second side and measuring a second baseline response of the renal vessel to the nerve stimulation on the first side, and performing a post-denervation measurement includes supplying nerve stimulation to the renal vessel from the first side and measuring a first post-denervation response of the renal vessel to the nerve stimulation on the second side, and supplying nerve stimulation to the renal vessel from the second side and measuring a second post-denervation response of the renal vessel to the nerve stimulation on the first side.

Referring to FIG. 4, the stimulation site 400 is on the proximal side (first side) of the denervation site 402, and the measurement site 404 is on the distal side (second side) of the denervation site 402. This configuration is used to record the first response (baseline or post-denervation). To record the second response (baseline or post-denervation), the stimulation site 400 and the measurement site 404 are swapped to opposite sides from the configuration shown in FIG. 4. According to the third approach, denervation verification test in both efferent and afferent directions is used to verify complete, bidirectional denervation.

In a specific embodiment, performing a baseline measurement includes supplying nerve stimulation to the renal vessel from a first location on the first side of the denervation location and measuring the first baseline response of the renal vessel to the nerve stimulation on a second location on the second side, and supplying nerve stimulation to the renal vessel from the second location and measuring the second baseline response of the renal vessel to the nerve stimulation at the first location. Performing a post-denervation measurement includes supplying nerve stimulation to the renal vessel from the first location and measuring the first post-denervation response of the renal vessel to the nerve stimulation at the second location, and supplying nerve stimulation to the renal vessel from the second location and measuring the second post-denervation response of the renal vessel to the nerve stimulation at the first location.

The heart and other muscles of the body generate noise that can interfere with subject verification. Various signal processing methods can be used to increase the signal-to-noise ratio of the detected signal (DS) resulting from the verification test stimulus. Measuring the first baseline response includes filtering the first baseline response to increase signal-to-noise ratio. Measuring the second baseline response includes filtering the second baseline response to increase signal-to-noise ratio. Measuring the first post-denervation response includes filtering the first baseline response to increase signal-to-noise ratio. Measuring the second post-denervation response includes filtering the second baseline response to increase signal-to-noise ratio. Various filtering techniques can be used, including the use of a band pass filter to filter out EKG noise and other background noise from the patient and the surroundings. In one example, a band pass filter in the range of about 500 to about 5,000 or up to about 10,000 Hz may be used.

One technique to improve signal-to-noise involves synchronizing the measurement with the electrocardiogram to include only DS signals that are recorded during electrically quiet times (e.g., ST segment). Cardiosynchronous processing of denervation test signals reduces the effect of cardiogenic noise. Denervation test signal epoch averaging of N epochs is used to improve signal-to-noise by $\sqrt{N}$. For instance, signal averaging of 400 signal epochs can improve signal-to-noise by a factor of 20. Measuring the first baseline response, measuring the second baseline response, measuring the first post-denervation response, and measuring the second post-denervation response each include synchronizing with electrocardiogram to substantially avoid detected signals other than detected signals that are recorded during electrically quiet times. For example, measuring the first baseline response, measuring the second baseline response, measuring the first post-denervation response, and measuring the second post-denervation response each include epoch averaging of multiple epochs relative to stimulus of the nerve stimulation to increase signal-to-noise ratio. The above filters are used to improve denervation test detected signal-to-noise ratio to improve the confidence of denervation verification.

Another feature is to limit the effect of stimulus polarization on the measurement. Since neural pulses travel many meters per second, it is necessary to sense the evoked neural response within microseconds after the stimulus. Polarization afterpotentials are minimized by using a bipolar or quadpolar or pentapolar stimulation pulse that has no DC content and tends to rapidly neutralize polarization effects.

In certain preferred embodiments, the nerve stimulation is multiphasic stimulation. Multiphasic stimuli tend to have little polarization afterpotential. The nerve stimulation is supplied via one or more electrodes made of low polarization electrode material. Low polarization stimulation electrodes are used to minimize polarization afterpotentials. Examples include Ag/AgCl, TiN, IrOx, and platinized platinum. For a discussion of identifying stimulus parameters and electrode geometries that were effective in selectively stimulating targeted neuronal populations within the central nervous system, see Cameron C. McIntyre & Warren M. Grill, "Selective Microstimulation of Central Nervous System Neurons," Annals of Biomedical Engineering. 2000; 28:219-233.

The nerve stimulation has a narrow pulse width selected to reduce or minimize stimulus polarization (e.g., about 50 microseconds). In one specific embodiment, the nerve stimulation has a pulse width substantially equal to chronaxie of the renal vessel. Chronaxie is the tissue-excitability parameter that permits choice of the optimum stimulus pulse duration for stimulation of any excitable tissue. When the chronaxie of nerve is measured, it is important to recognize that most nerve trunks contain bundles of fibers having different diameters and hence different propagation velocities, and with each fiber group having its own chronaxie. A strength-duration curve can be plotted for each fiber group, from which the chronaxies can be determined. See Leslie A. Geddes, "Accuracy Limitations of Chronaxie Values," IEEE Transactions on Biomedical Engineering. January 2004; 51(1):176-181.

Exemplary Systems

Figure 6:
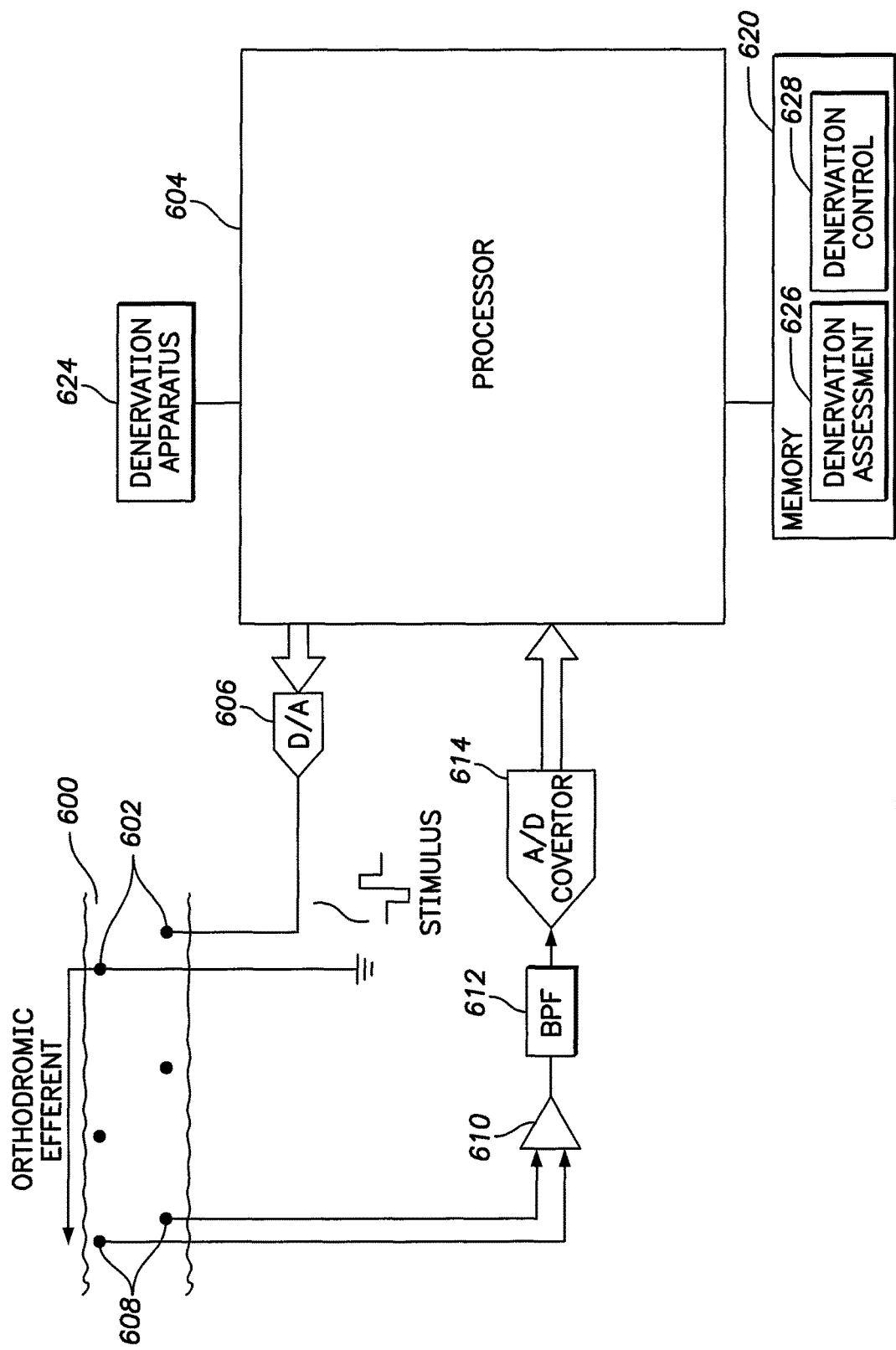
FIG. 6 is a schematic diagram illustrating an example of a denervation system with denervation verification and feedback.

FIG. 6 is a schematic diagram illustrating an example of a denervation system with denervation verification and feedback. A renal vessel 600 may include efferent nerves for efferent conduction and/or afferent nerves for afferent in the directions shown. Note that when a nerve is stimulated, it will conduct in both directions regardless of whether the nerve is efferent or afferent. Therefore, one may characterize one direction of conduction as orthodromic (e.g., in the normal direction for that nerve) instead of efferent and the opposite direction of conduction as antidromic (e.g., in the direction opposite the normal direction for that nerve) instead of afferent.

In FIG. 6, a pair of stimulating electrodes 602 are provided to stimulate efferent nerves or nerves for orthodromic and efferent conduction (e.g., with the stimulus as shown) under the control of a processor 604 via a D/A converter 606, and another pair of detecting or measurement electrodes 608 are provided to record nerve plexus electrical activity to determine whether there is orthodromic or efferent conduction. The measurement electrodes 608 are coupled via an amplifier 610 (e.g., having a $10^5$ gain), a band pass filter or BPF 612 (e.g., about 500-10,000 Hz), and an A/D converter 614 to the processor 604. The processor 604 has circuitries and/or executes software modules stored in memory 620 in order to control the nerve stimulating and measuring and to control operation of a denervation apparatus 624 for denervating at least some tissue proximate the renal vessel 600 at a location between the stimulating electrodes 602 and the measurement electrodes 608 (e.g., in the form of ablation electrodes on the nerves). The denervation apparatus 624 may include, for example, a denervation member in the form of one or more RF electrodes and an RF energy source. For illustrative purposes, FIG. 6 shows a denervation assessment module 626 to assess denervation of the renal vessel based on a comparison of the baseline measurement and the post-denervation measurement of renal nerve plexus electrical activity at the renal vessel 600 and a denervation control module 628 to control the nerve denervation by the denervation apparatus 624. If a target denervation of the renal vessel 600 is not achieved, the denervation control module 628 instructs operation of the denervation apparatus 624 to repeat denervating at least some tissue proximate the renal vessel, instructs operation of the measurement electrodes 608 to repeat performing a post-denervation measurement, and instructs the denervation assessment module 626 to repeat assessing denervation of the renal vessel 600, until the target denervation of the renal vessel 600 is achieved.

The denervation system in FIG. 6 can be used to carry out the procedure of the first approach (without activating the stimulating electrodes 602), the procedure of the second approach, and partially the procedure of the third approach (with the need to swap the stimulating and measuring positions). A denervation system that is more suitable for the third approach is shown in FIG. 7.

It will be understood by those of ordinary skill in the art that the various methods and systems described herein can be performed either intravascularly, extravascularly, or a combination approach using both intravascular and extravascular approaches in combination. In the intravascular approach, a suitable ablation catheter is advanced through the patient's vasculature and into the renal artery adjacent the afferent and efferent renal nerves.

Figure 7:
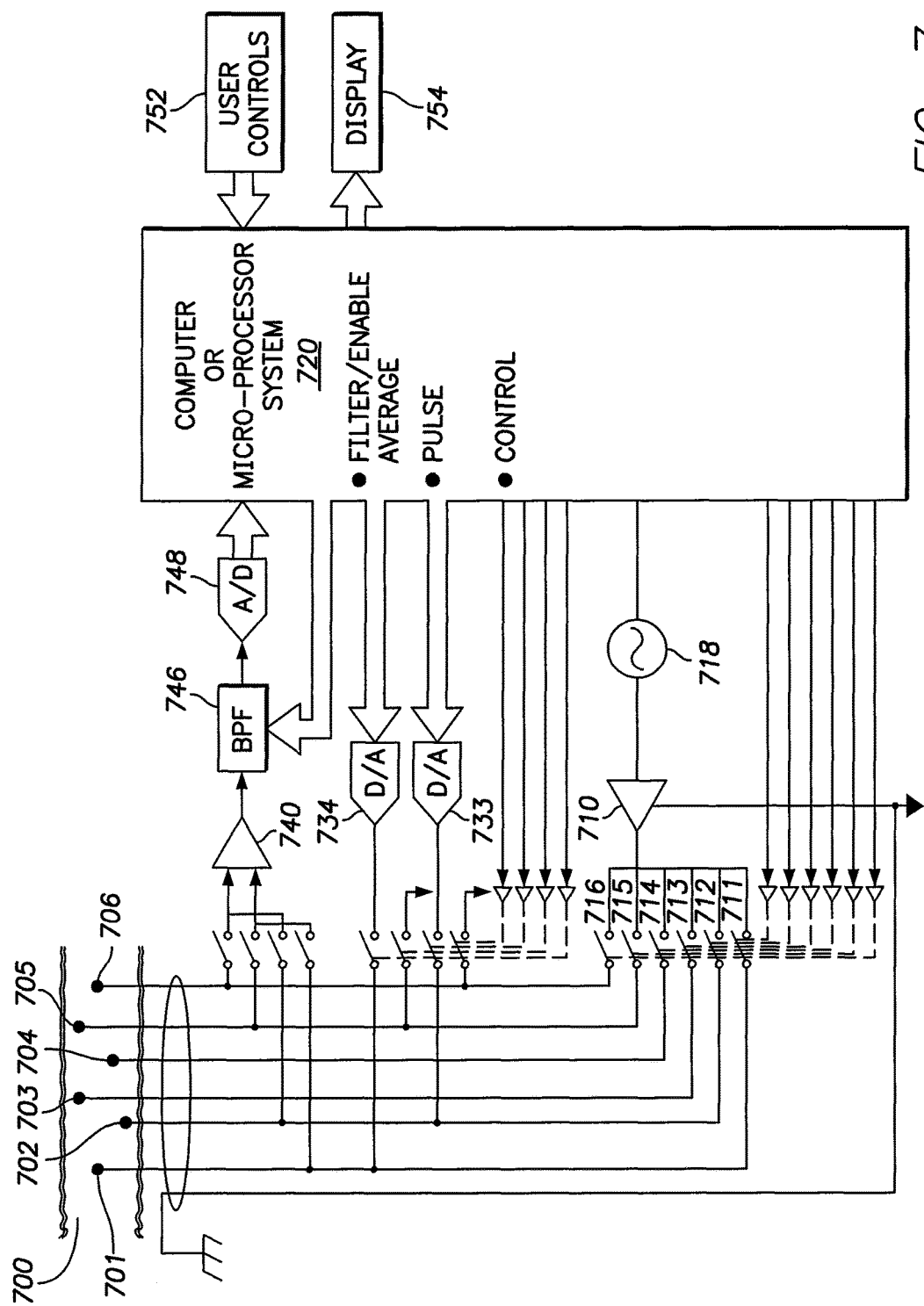
FIG. 7 is a schematic diagram illustrating another example of a denervation system with denervation verification and feedback.

FIG. 7 is a schematic diagram illustrating another example of a denervation system with denervation verification and feedback. A renal vessel 700 has coupled thereto a plurality of electrodes 701-706. FIG. 7 shows a 6-electrode system, but the number of electrodes can vary in other embodiments. In FIG. 7, all six electrodes are used for ablation, while two pairs of electrodes 701-702 and 705-706 are alternately used for stimulating and measuring to perform denervation verification. Denervation by ablation is performed by connecting an RF amplifier 710 via leads to the six electrodes 701-706 in sequence using six switches 711-716 which are connected to the output of the RF amplifier 710 and an RF oscillator 718 and controlled by a computer or controller 720. The computer 720 has a processor, a memory, and various circuitries and modules to control denervation of the renal vessel 700 and perform denervation verification and feedback, including pulse generation, signal control, switch control, filtering, signal averaging, etc. For example, the computer 720 may include a denervation assessment module and a denervation control module such as those shown in FIG. 6.

After ablation, inactivation of the renal nerves of the renal vessel 700 is verified by stimulating a pair of electrodes 701-702 or 705-706 (bipolarly or unipolarly), alternately, using D/A converters 733, 734 and switches connected to their outputs (pairs of switches corresponding to pairs of stimulating electrodes 701-702 and 705-706), and by "listening" for a conducted signal by selecting a pair of electrodes 705-706 or 701-702, alternately, to connect to a measurement amplifier 740 via switches (pairs of switches corresponding to pairs of measurement electrodes 705-706 and 701-702). The measurement amplifier 740 is connected to an analog or digital band pass filter or BPF 746 or directly to an A/D converter 748 that is read by the computer 720. The BPF 746 can be eliminated if such filtering is done in the computer 720. A control panel for the system may include user controls 752 and display 754. According to the third approach, the denervation assessment module in the computer 720 contains an algorithm to analyze the response "seen" by the measurement amplifier 740 and decides if the renal nerves are blocked and the stimulation/response verification can be performed on different electrodes to assure all nerves are blocked. If more ablation is needed, the denervation control module in the computer 720 can advise the user or perform additional ablation automatically until there is no afferent or efferent nerve signal continuity.

In the description, numerous details are set forth for purposes of explanation in order to provide a thorough understanding of the present invention. However, it will be apparent to one skilled in the art that not all of these specific details are required in order to practice the present invention. It is also noted that the invention may be described as a process, which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged.

From the foregoing, it will be apparent that the invention provides methods, apparatuses and programs stored on computer readable media for renal denervation verification and feedback. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. A renal denervation feedback method comprising:
    performing a baseline measurement of intrinsic renal nerve plexus electrical activity at a renal vessel by monitoring compound action potentials including baseline afferent and efferent signals;
    denervating at least some tissue proximate the renal vessel after performing the baseline measurement;
    performing a post-denervation measurement of intrinsic renal nerve plexus electrical activity at the renal vessel by monitoring post-denervation compound action potentials including post-denervation afferent and efferent signals, after the denervating;
    assessing denervation of the renal vessel based on a comparison of the baseline measurement and the post-denervation measurement of renal nerve plexus electrical activity at the renal vessel; and
    determining the denervation is complete when the post-denervation compound action potentials include afferent signals below a threshold value.

2. The renal denervation feedback method of claim 1, further comprising, if the denervation is not complete:
    repeating the steps of denervating, performing a post-denervation measurement, and assessing denervation of the renal vessel until the post-denervation compound action potentials are solely efferent signals.

3. The renal denervation feedback method of claim 2, wherein repeating the steps of denervating, performing a post-denervation measurement, and assessing denervation of the renal vessel comprises:
    adjusting a level of denervation for denervating at least some tissue proximate the renal vessel based on a result of assessing denervation of the renal vessel.

4. The renal denervation feedback method of claim 1, wherein performing the baseline measurement of renal nerve plexus electrical activity comprises:
    counting a number of baseline afferent spikes each representing an afferent compound action potential that exceeds a preset threshold during a specified period of time; and
    counting a number of baseline efferent spikes each representing an efferent compound action potential that exceeds the preset threshold during the specified period of time, and
wherein performing a post-denervation measurement of renal nerve plexus electrical activity comprises:
    counting a number of post-denervation afferent spikes each representing an afferent compound action potential that exceeds the preset threshold during the specified period of time; and
    counting a number of post-denervation efferent spikes each representing an efferent compound action potential that exceeds the preset threshold during the specified period of time.

5. The renal denervation feedback method of claim 1,
wherein performing a baseline measurement comprises supplying nerve stimulation to the renal vessel from one side of a denervation location for denervating at least some tissue proximate the renal vessel and measuring a baseline response of the renal vessel to the nerve stimulation on an opposite side of the denervation location; and
wherein performing a post-denervation measurement comprises supplying nerve stimulation to the renal vessel from one side of the denervation location and measuring a post-denervation response of the renal vessel to the nerve stimulation on an opposite side of the denervation location.

6. The renal denervation feedback method of claim 1, wherein monitoring compound action potentials including baseline afferent and efferent signals comprises using a plurality of bi-polar measurement electrodes to measure the baseline afferent and efferent signals.

7. The renal denervation feedback method of claim 1, wherein monitoring compound action potentials including post-denervation afferent and efferent signals comprises using a plurality of bi-polar measurement electrodes to measure the post-denervation afferent and efferent signals.

8. The renal denervation feedback method of claim 1, wherein denervating at least some tissue proximate the renal vessel after performing the baseline measurement comprises using at least one denervation electrode to denervate the at least some tissue.

9. A renal denervation feedback system comprising:
   at least one denervation member to denervate at least some tissue proximate the renal vessel;
   at least one measurement member to perform a baseline measurement of intrinsic renal nerve plexus electrical activity, including baseline afferent and efferent signals, at a renal vessel before denervation of at least some tissue proximate the renal vessel and to perform a post-denervation measurement of renal nerve plexus electrical activity, including post-denervation afferent and efferent signals, at the renal vessel after the denervation, the baseline and post-denervation measurements acquired by monitoring compound action potentials; and
   a denervation assessment module to assess denervation of the renal vessel based on a comparison of the baseline measurement and the post-denervation measurement of renal nerve plexus electrical activity at the renal vessel, wherein the denervation assessment module is configured to determine the denervation is complete when the post-denervation compound action potentials include afferent signals below a threshold value.

10. The renal denervation system of claim 9, wherein, if the denervation is not complete, the denervation assessment module is further configured to direct the at least one denervation member to repeat denervation of the at least some tissue.

11. The renal denervation system of claim 10, wherein the denervation assessment module is further configured to direct the at least one denervation member to adjust a level of denervation for denervating the at least some tissue proximate the renal vessel.

12. The renal denervation system of claim 9,
   wherein the at least one measurement member is configured to perform the baseline measurement of renal nerve plexus electrical activity by:
      counting a number of baseline afferent spikes each representing an afferent compound action potential that exceeds a preset threshold during a specified period of time; and
      counting a number of baseline efferent spikes each representing an efferent compound action potential that exceeds the preset threshold during the specified period of time, and
   wherein the at least one measurement member is configured to perform the post-denervation measurement of renal nerve plexus electrical activity by:
      counting a number of post-denervation afferent spikes each representing an afferent compound action potential that exceeds the preset threshold during the specified period of time; and
      counting a number of post-denervation efferent spikes each representing an efferent compound action potential that exceeds the preset threshold during the specified period of time.

13. The renal denervation feedback system of claim 9, wherein the at least one measurement member comprises a plurality of bi-polar measurement electrodes.

14. The renal denervation feedback system of claim 9, wherein the at least one denervation member comprises at least one denervation electrode.

* * * * *